(12) United States Patent
Stölting et al.

(10) Patent No.: US 7,026,307 B2
(45) Date of Patent: Apr. 11, 2006

(54) METHOD FOR PRODUCING 1,3-DISUBSTITUTED 2-NITROGUANIDINES

(75) Inventors: Jörn Stölting, Köln (DE); Kai van Laak, Wolfenbüttel (DE); Wolfram Sirges, Düsseldorf (DE); Armin Heyn, Bergisch Gladbach (DE); Torsten Taschner, Köln (DE)

(73) Assignee: Bayer CropScience AG, Monheim (DE)

( * ) Notice: Subject to any disclaimer, the term of this patent is extended or adjusted under 35 U.S.C. 154(b) by 139 days.

(21) Appl. No.: 10/476,599

(22) PCT Filed: Apr. 24, 2002

(86) PCT No.: PCT/EP02/04474

§ 371 (c)(1),
(2), (4) Date: Mar. 22, 2004

(87) PCT Pub. No.: WO02/090331

PCT Pub. Date: Nov. 14, 2002

(65) Prior Publication Data

US 2004/0167177 A1 Aug. 26, 2004

(30) Foreign Application Priority Data

May 3, 2001 (DE) ................ 101 21 652

(51) Int. Cl.
*A01N 43/00* (2006.01)
*A61K 31/33* (2006.01)

(52) U.S. Cl. ............. 514/183; 514/342; 514/365; 514/408; 546/269.1; 546/332; 548/203; 548/566; 544/215; 544/241

(58) Field of Classification Search ........... 514/342, 514/365, 408, 183; 546/269.1, 332; 548/203, 548/566; 544/215, 241
See application file for complete search history.

(56) References Cited

U.S. PATENT DOCUMENTS

| | | | |
|---|---|---|---|
| 5,032,589 A | 7/1991 | Shiokawa et al. | 514/245 |
| 5,034,404 A | 7/1991 | Uneme et al. | 514/365 |
| 5,034,524 A | 7/1991 | Shiokawa et al. | 544/124 |
| 5,051,434 A | 9/1991 | Kozo et al. | 514/357 |
| 5,084,467 A | 1/1992 | Shiokawa et al. | 514/357 |
| 5,204,359 A | 4/1993 | Shiokawa et al. | 514/332 |
| 5,238,949 A | 8/1993 | Shiokawa et al. | 514/327 |
| 5,489,603 A | 2/1996 | Uneme et al. | 514/365 |
| 5,633,375 A | 5/1997 | Uneme et al. | 544/336 |
| 5,719,146 A | 2/1998 | Shiokawa et al. | 514/229.2 |
| RE35,811 E | 5/1998 | Shiokawa et al. | 514/357 |
| 6,187,773 B1 | 2/2001 | Wu et al. | 514/245 |
| 6,194,575 B1 | 2/2001 | Wollweber et al. | 544/180 |
| 6,232,309 B1 | 5/2001 | Shiokawa et al. | 514/222.5 |
| 6,344,453 B1 | 2/2002 | Shiokawa et al. | 514/223.8 |
| 2001/0046994 A1 | 11/2001 | Wu et al. | 514/241 |

FOREIGN PATENT DOCUMENTS

| | | |
|---|---|---|
| CA | 2052731 | 4/1992 |
| EP | 0 483 062 | 4/1992 |
| JP | 3-291267 | 12/1991 |
| JP | 03291267 | * 12/1991 |
| JP | 10-67766 | 3/1998 |
| JP | 10-147580 | 6/1998 |
| JP | 10147580 | * 6/1998 |
| JP | 11092463 | * 6/1999 |
| WO | 99/09009 | 2/1999 |

OTHER PUBLICATIONS

**Warnhoff, H. et al.: "Photodegradation of Imidacloprid" J. Agric. Food Chem., Bd. 47, 1999, Seiten 1730-1734, XP002212770 Beispiel 4.
**Kagabu, S. et al.: "5-Azidoimidacloprid and an Acyclic Analogue as Candidate Photoaffinity Probes for Mammalian and Insect Nicotinic Acetlcholine Receptors" J. Med. Chem., Bd. 43, 2000, Seiten 5003-5009, XP002212771 Seite 5005; Abbildung 3; Beispiel 2.

(Continued)

*Primary Examiner*—Johann Richter
*Assistant Examiner*—Chukwuma Nwaonicha
(74) *Attorney, Agent, or Firm*—Richard E. L. Henderson; Raymond J. Harmuth

(57) ABSTRACT

The present invention relates to a process for the preparation of compounds of the formula (I)

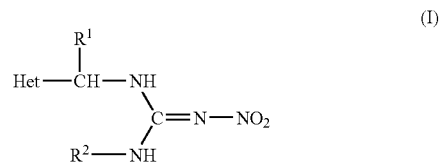

by reacting compounds of the formula (II)

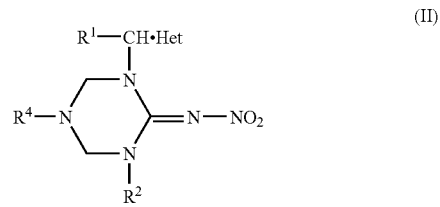

in which
$R^1$, $R^2$, $R^4$ and Het are as defined in the description, with anhydrous hydrogen halide in the presence of a nitrile.

15 Claims, No Drawings

OTHER PUBLICATIONS

**Maienfisch, P. et al.: "A novel method for the preparation of N,N'-disubstituted N'-nitroguanidines, including a parctical synthesis of the neonicotinoid clothianidin" Tetrahedron Letters, Bd. 41, 2000, Seiten 7187-7191, XP002212772 Seite 7189; Abbildung 2.

* cited by examiner

METHOD FOR PRODUCING 1,3-DISUBSTITUTED 2-NITROGUANIDINES

The present invention relates to a novel process for the preparation of 1,3-disubstituted 2-nitroguanidines.

EP-A-0 483 062 discloses a process for the preparation of 1,3-disubstituted 2-nitroguanidines. They are obtained by hydrolysis of corresponding 2-nitroimino-1,3,5-triazacyclohexane derivatives. The hydrolysis is preferably carried out in the presence of strong mineral acids or organic acids.

Disadvantages of this process are the long reaction times and the formation of secondary products, which make it necessary to subject the desired end-products to a complex cleaning operation.

Moreover, as is known, when working in the presence of aqueous strong acids, measures must be taken to protect, for example the reactors, from corrosion.

JP 3291267, JP 10067766, JP 10147580 and WO 99/09009 relate to similar processes.

The object of the present invention was to provide an improved process for the preparation of 1,3-disubstituted 2-nitroguanidines.

The present invention provides a process for the preparation of compounds of the formula (I)

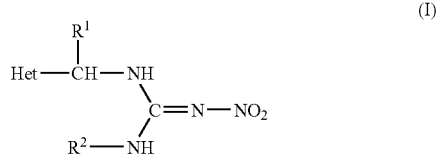

in which
$R^1$ is hydrogen or $C_1$–$C_4$-alkyl,
$R^2$ is hydrogen, $C_1$–$C_6$-alkyl, $C_3$–$C_6$-cycloalkyl or a radical —$CH_2R^3$,
$R^3$ is $C_2$–$C_5$-alkenyl, $C_2$–$C_5$-alkinyl, phenyl, cyanophenyl, nitrophenyl, halogenophenyl having from 1 to 3 halogen atoms; phenyl substituted by $C_1$–$C_3$-alkyl, $C_1$–$C_3$-halogenoalkyl having from 1 to 7 halogen atoms, $C_1$–$C_3$-alkoxy or $C_1$–$C_3$-halogenoalkoxy having from 1 to 7 halogen atoms; 5-thiazolyl substituted by one to two (preferably one) substituents from the group consisting of $C_1$–$C_3$-alkyl, $C_1$–$C_3$-halogenoalkyl having from 1 to 7 halogen atoms, cyclopropyl, halogenocyclopropyl having from 1 to 3 halogen atoms, $C_2$–$C_3$-alkenyl, $C_2$–$C_3$-alkinyl, $C_1$–$C_3$-alkoxy, $C_2$–$C_3$-halogenoalkenyl having from 1 to 5 halogen atoms, $C_2$–$C_3$-halogenoalkinyl having from 1 to 3 halogen atoms, $C_1$–$C_3$-halogenoalkoxy having from 1 to 7 halogen atoms, $C_1$–$C_3$-alkylthio, $C_1$–$C_3$-halogenoalkylthio having from 1 to 7 halogen atoms, allyloxy, propargyloxy, allylthio, propargylthio, halogenoallyloxy having from 1 to 5 halogen atoms, halogenoallylthio having from 1 to 5 halogen atoms, halogen, cyano or nitro; or 3-pyridyl substituted by one to four (preferably one or two) radicals from the group consisting of $C_1$–$C_3$-halogenoalkyl having from 1 to 7 halogen atoms, cyclopropyl, halogenocyclopropyl having from 1 to 3 halogen atoms, $C_2$–$C_3$-alkenyl, $C_2$–$C_3$-alkinyl, $C_2$–$C_3$-halogenoalkenyl having from 1 to 5 halogen atoms, $C_2$–$C_3$-halogenoalkinyl having from 1 to 3 halogen atoms, $C_1$–$C_3$-halogenoalkoxy having from 1 to 7 halogen atoms, $C_1$–$C_3$-alkylthio, $C_1$–$C_3$-halogenoalkylthio having from 1 to 7 halogen atoms, allyloxy, propargyloxy, allylthio, propargylthio, halogenoallyloxy having from 1 to 5 halogen atoms, halogenoallylthio having from 1 to 5 halogen atoms, cyano, nitro, $C_1$–$C_3$-alkyl, $C_1$–$C_3$-alkoxy or halogen, Het is an unsubstituted or substituted aromatic or non-aromatic, monocyclic or bicyclic heterocyclic radical, preferably from the series

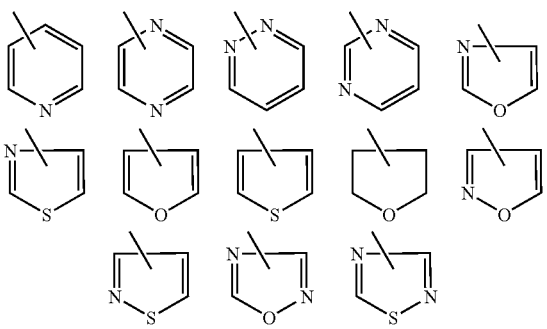

which may include one or two substituents from the group consisting of $C_1$–$C_3$-halogenoalkyl having from 1 to 7 halogen atoms, cyclopropyl, halogenocyclopropyl having from 1 to 3 halogen atoms, $C_2$–$C_3$-alkenyl, $C_2$–$C_3$-alkinyl, $C_2$–$C_3$-halogenoalkenyl having from 1 to 5 halogen atoms, $C_2$–$C_3$-halogenoalkinyl having from 1 to 3 halogen atoms, $C_1$–$C_3$-halogenoalkoxy having from 1 to 7 halogen atoms, $C_1$–$C_3$-alkylthio, $C_1$–$C_3$-halogenoalkylthio having from 1 to 7 halogen atoms, allyloxy, propargyloxy, allylthio, propargylthio, halogenoallyloxy having from 1 to 5 halogen atoms, halogenoallylthio having from 1 to 5 halogen atoms, cyano, nitro, $C_1$–$C_3$-alkyl, $C_1$–$C_3$-alkoxy and halogen, characterized in that a compound of the formula (II)

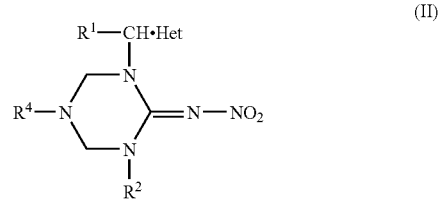

in which
$R^1$, $R^2$ and Het are as defined above, and
$R^4$ is $C_1$–$C_{10}$-alkyl, $C_3$–$C_6$-cycloalkyl, phenyl, arylalkyl or heterocyclylmethyl, each of which may be unsubstituted or substituted, where heterocyclyl is an unsaturated or saturated 5- or 6-membered heterocycle containing one or more heteroatoms from the series nitrogen, oxygen and sulphur, such as, for example, furan, tetrahydrofuran, thiophene or pyridine, in the presence of a nitrile having from 3 to 5 carbon atoms, is reacted with anhydrous hydrogen halide.

The compounds of the formula (I) can also be in the form of double-bond isomers as regards the —N=C(2) bond and in their tautomeric forms (formulae Ia, Ib):

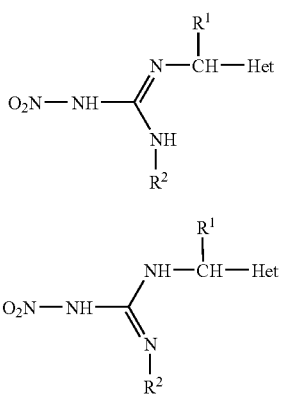

Formula (I) is accordingly to be taken to mean that it also includes the corresponding double-bond isomers and the formulae (Ia) and (Ib).

Surprisingly, the process according to the invention produces, selectively and in high yields, the end-products of the formula (I) in pure form after a short reaction time under mild reaction conditions.

A particular advantage of the process according to the invention is the use of the nitrile since, upon cooling the reaction mixture, the end product directly crystallizes out and can thus be isolated in a simple manner.

For example, using 1-(2-chlorothiazol-5-ylmethyl)-2-nitro-imino-5-benzyl-3-methyl-1,3,5-tria zacyclohexane as starting material and anhydrous hydrogen chloride and butyronitrile, the course of the process according to the invention can be shown by the following equation:

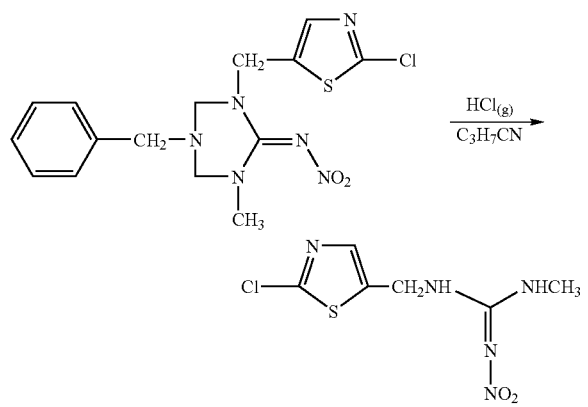

The compounds required as starting materials for the process according to the invention are generally defined by the formula (II).

Preferred substituents and ranges of the radicals listed in the formulae mentioned above and below are illustrated below:

$R^1$ is preferably hydrogen, methyl, ethyl, n- or i-propyl.

$R^2$ is preferably hydrogen, methyl, ethyl, n-propyl, i-propyl or n-butyl, cyclopropyl, cyclopentyl, cyclohexyl or a radical —$CH_2R^3$.

$R^3$ is preferably $C_2$–$C_5$-alkenyl, $C_2$–$C_5$-alkinyl, phenyl, cyanophenyl, nitrophenyl, halogenophenyl having from 1 to 3 halogen atoms; phenyl substituted by $C_1$–$C_3$-alkyl, $C_1$–$C_3$-halogenoalkyl having from 1 to 7 halogen atoms, $C_1$–$C_3$-alkoxy or $C_1$–$C_3$-halogenoalkoxy having from 1 to 7 halogen atoms; 5-thiazolyl substituted by one to two (preferably one) substituents from the group consisting of $C_1$–$C_3$-alkyl, $C_1$–$C_3$-halogenoalkyl having from 1 to 7 halogen atoms, cyclopropyl, halogenocyclopropyl having from 1 to 3 halogen atoms, $C_2$–$C_3$-alkenyl, $C_2$–$C_3$-alkinyl, $C_1$–$C_3$-alkoxy, $C_2$–$C_3$-halogenoalkenyl having from 1 to 5 halogen atoms, $C_2$–$C_3$-halogenoalkinyl having from 1 to 3 halogen atoms, $C_1$–$C_3$-halogenoalkoxy having from 1 to 7 halogen atoms, $C_1$–$C_3$-alkylthio, $C_1$–$C_3$-halogenoalkylthio having from 1 to 7 halogen atoms, allyloxy, propargyloxy, allylthio, propargylthio, halogenoallyloxy having from 1 to 5 halogen atoms, halogenoallylthio having from 1 to 5 halogen atoms, halogen, cyano or nitro; or 3-pyridyl substituted by one to two (preferably one) radicals from the group consisting of $C_1$–$C_3$-halogenoalkyl having from 1 to 7 halogen atoms, cyclopropyl, halogenocyclopropyl having from 1 to 3 halogen atoms, $C_2$–$C_3$-alkenyl, $C_2$–$C_3$-alkinyl, $C_2$–$C_3$-halogenoalkenyl having from 1 to 5 halogen atoms, $C_2$–$C_3$-halogenoalkinyl having from 1 to 3 halogen atoms, $C_1$–$C_3$-halogenoalkoxy having from 1 to 7 halogen atoms, $C_1$–$C_3$-alkylthio, $C_1$–$C_3$-halogenoalkylthio having from 1 to 7 halogen atoms, allyloxy, propargyloxy, allylthio, propargylthio, halogenoallyloxy having from 1 to 5 halogen atoms, halogenoallylthio having from 1 to 5 halogen atoms, cyano, nitro, $C_1$–$C_3$-alkyl, $C_1$–$C_3$-alkoxy or halogen.

$R^4$ is preferably unsubstituted $C_1$–$C_{10}$-alkyl or $C_1$–$C_{10}$-alkyl substituted by from 1 to 6 radicals from the group consisting of halogen, hydroxyl, $C_1$–$C_4$-alkoxy, $C_1$–$C_4$-halogenoalkoxy having from 1 to 9 halogen atoms, di-($C_1$–$C_4$-alkyl)-amino or $C_1$–$C_5$-alkoxycarbonyl; unsubstituted $C_3$–$C_6$-cycloalkyl or $C_3$–$C_6$-cycloalkyl substituted by from 1 to 4 radicals from the series $C_1$–$C_4$-alkyl or halogen; in each case unsubstituted phenyl, benzyl or heterocyclylmethyl, or phenyl, benzyl or heterocyclylmethyl each substituted by from 1 to 3 ring substituents from the group consisting of halogen, $C_1$–$C_4$-alkyl, $C_1$–$C_4$-halogenoalkyl having from 1 to 9 halogen atoms, $C_1$–$C_4$-alkoxy, $C_1$–$C_4$-halogenoalkoxy having from 1 to 9 halogen atoms, $C_1$–$C_4$-alkylthio, nitro or cyano, where heterocyclyl is an unsaturated or saturated 5- or 6-membered heterocycle having one or two (preferably one) heteroatoms from the series nitrogen, oxygen and sulphur, such as, for example, furan, tetrahydrofuiran, thiophene or pyridine.

Het is preferably an unsubstituted or mono- or disubstituted (preferably monosubstituted) heterocyclic radical from the series

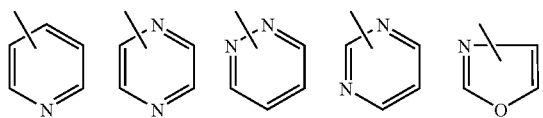

-continued

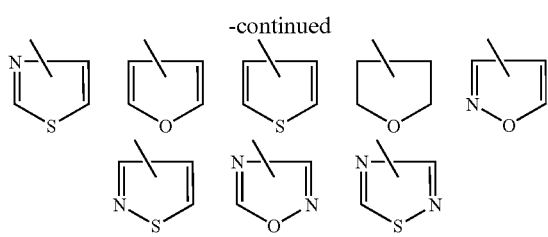

in particular

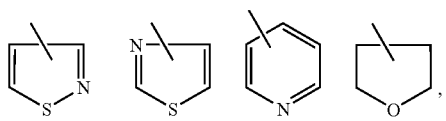

the substituents preferably being chosen from the series fluorine, chlorine, bromine, methyl, ethyl, methoxy and ethoxy.

$R^1$ is particularly preferably hydrogen, methyl or ethyl.

$R^2$ is particularly preferably hydrogen, methyl, ethyl, n-propyl, i-propyl, n-butyl, cyclopropyl, cyclopentyl, cyclohexyl or a radical —$CH_2R^3$.

$R^3$ is particularly preferably $C_2$–$C_3$-alkenyl, $C_2$–$C_3$-alkinyl, phenyl, cyano-phenyl, nitrophenyl, halogenophenyl having from 1 to 3 halogen atoms; phenyl substituted by $C_1$–$C_3$-alkyl, $C_1$–$C_3$-halogenoalkyl having from 1 to 7 halogen atoms, $C_1$–$C_3$-alkoxy or $C_1$–$C_3$-halogenoalkoxy having from 1 to 7 halogen atoms; 5-thiazolyl or 3-pyridyl each substituted by one or two (preferably one) substituents from the group consisting of $C_1$–$C_3$-alkyl, $C_1$–$C_3$-halogenoalkyl having from 1 to 7 halogen atoms, $C_1$–$C_3$-alkoxy, $C_1$–$C_3$-halogenoalkoxy having from 1 to 7 halogen atoms, $C_1$–$C_3$-alkylthio, $C_1$–$C_3$-halogenoalkylthio having from 1 to 7 halogen atoms, halogen, cyano or nitro.

$R^4$ is particularly preferably $C_1$–$C_{10}$-alkyl; $C_1$–$C_8$-alkyl, substituted by from 1 to 6 radicals from the group consisting of halogen, $C_1$–$C_4$-alkoxy and $C_1$–$C_4$-halogenoalkoxy having from 1 to 9 halogen atoms; unsubstituted $C_3$–$C_6$-cycloalkyl or $C_3$–$C_6$-cycloalkyl substituted by 1 or 2 radicals from the series methyl, ethyl, fluorine and chlorine; unsubstituted phenyl, benzyl or heterocyclylmethyl, or phenyl, benzyl or heterocyclyl each substituted by from 1 to 3 ring substituents from the group consisting of halogen, $C_1$–$C_4$-alkyl, $C_1$–$C_4$-halogenoalkyl having from 1 to 9 halogen atoms, $C_1$–$C_4$-alkoxy, $C_1$–$C_4$-halogenoalkoxy having from 1 to 9 halogen atoms, $C_1$–$C_4$-alkylthio, nitro or cyano, where heterocyclyl is an unsaturated or saturated 5- or 6-membered heterocycle containing one heteroatom from the series nitrogen, oxygen and sulphur, such as, for example, furan, tetrahydrofuran, thiophene or pyridine.

Het is particularly preferably thiazolyl, pyridyl or tetrahydrofuranyl, each of which may be unsubstituted or mono- or disubstituted (in particular monosubstituted), the substituents being chosen from the series fluorine, chlorine, methyl and methoxy.

$R^1$ is very particularly preferably hydrogen, methyl or ethyl, especially hydrogen.

$R^2$ is very particularly preferably hydrogen, methyl, ethyl, n-propyl, i-propyl, n-butyl, cyclopropyl, cyclopentyl, allyl, propargyl, benzyl, p-chlorobenzyl, 3-pyridylmethyl or 6-chloro-3-pyridylmethyl.

$R^4$ is very particularly preferably methyl, ethyl, n-propyl, cyclopropyl, cyclopentyl, cyclohexyl, phenyl, benzyl or furfuryl.

Het is very particularly preferably one of the radicals

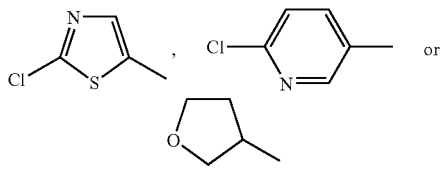

In all of the general radical definitions and in the preferred ranges, halogen (atoms) are preferably F, Cl, Br, I, in particular F, Cl, Br and especially F, Cl.

Particularly preferred starting materials for the process according to the invention are compounds of the formula (IIa), (IIb) and (IIc)

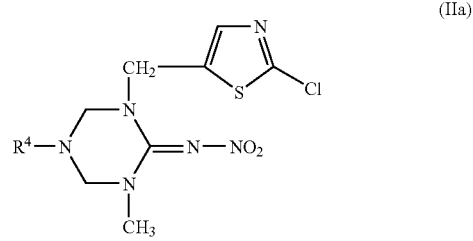

(IIa)

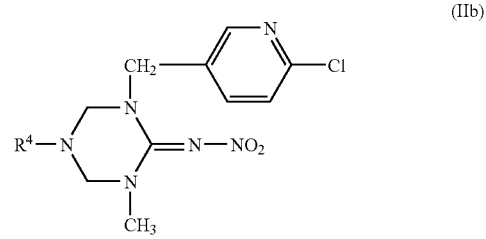

(IIb)

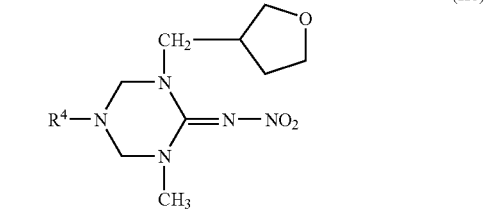

(IIc)

in which $R^4$ is methyl, ethyl, cyclopropyl, cyclopentyl, benzyl or furfuryl, where, of these, methyl, benzyl and furfuryl are in turn preferred.

The end-products of the process according to the invention are, when a compound of the formula (IIa) is used, the following compound

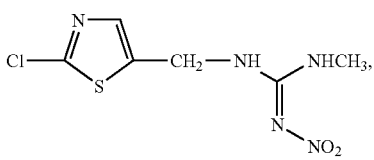

when a compound of the formula (IIb) is used, the following compound

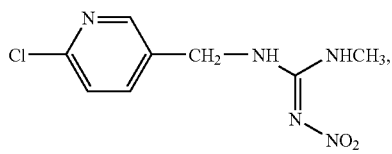

and when a compound of the formula (IIc) is used, the following compound

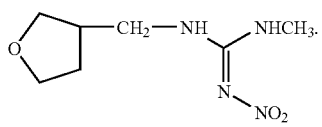

The radical definitions and explanations given in general terms above or listed in the preferred ranges can be combined with one another as desired, i.e. also between the respective ranges and preferred ranges. They apply to the end-products and also to the precursors and intermediates.

The term alkyl in this connection is also taken to mean the branched isomers, e.g. t-butyl for $C_4$-alkyl.

Preference is given to using those compounds of the formula (II) which have a combination of the preferred meanings given above in the process according to the invention.

Particular preference is given to using those compounds of the formula (II) which have a combination of the particularly preferred meanings given above in the process according to the invention.

Very particular preference is given to using those compounds of the formula (II) which have a combination of the very particularly preferred meanings given above in the process according to the invention.

The starting materials of the formula (II) are known or can be prepared by known processes (cf. EP-A-0 483 062, JP 3 291 267, EP-A-0 483 055, EP-A-0 428 941, EP-A-0 386 565, WO 98/42690).

The process according to the invention is carried out in the presence of a nitrile having from 3 to 5 carbon atoms.

Suitable nitriles are aliphatic mono- and dinitriles having from 3 to 5 carbon atoms. Propionitrile, butyronitrile, valeronitrile, malononitrile, succinonitrile, glutaronitrile can preferably be used. Propionitrile or butyronitrile are particularly preferably used, very particularly preferably butyronitrile.

It is also possible to use mixtures of the specified nitriles.

The process according to the invention is carried out at temperatures between −10° C. and 200° C., preferably between 20° C. and 150° C., particularly preferably between 40° C. and 80° C.

The process according to the invention is generally carried out under atmospheric pressure. However, it is also possible for the process to be carried out under elevated pressure.

Anhydrous hydrogen halide is used as reagent in the process according to the invention. Hydrogen chloride, hydrogen bromide or hydrogen iodide can preferably be used, particularly preferably hydrogen chloride or hydrogen bromide, very particularly preferably hydrogen chloride. The anhydrous hydrogen halide is preferably used in gaseous form.

The hydrogen halide is generally used in a molar ratio of from 0.5:1 to 10:1, preferably 1:1 to 6:1, based on the starting compound of the formula (II).

The reaction is generally carried out by bringing the starting material of the formula (II) in a nitrile to the desired temperature and gradually metering in the hydrogen halide over the course of the reaction.

To work-up, after cooling, water and/or sodium hydroxide solution is added where necessary, and the end-product, optionally after evaporating the mixture, is isolated, for example by filtration or extraction.

The compounds of the formula (I) prepared according to the invention are useful active ingredients in pest control. In particular, the compounds of the formula (I) are suitable for controlling insects and arachnids, which are encountered in useful and ornamental plants in agriculture, in particular, cotton, vegetable and fruit plantations, in forests, in the protection of stored products and materials and in the hygiene sector, in particular on pets and useful animals (see e.g. EP-A-0 376 279, EP-A-0 375 907, EP-A-0 383 091).

PREPARATION EXAMPLES

Preparation of 1-(2-chlorothiazol-5-ylmethyl)-2-nitro-3-methylguanidine

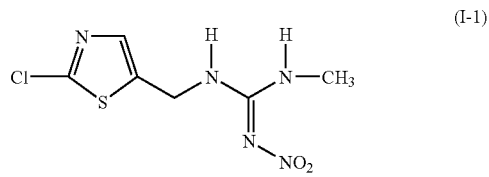

(I-1)

Example 1

22.1 g (0.05 mol) of 1-(2-chlorothiazol-5-ylmethyl)-2-nitro-imino-5-benzyl-3-methyl-1,3,5-triazacyclohexane (86.1% strength according to ISTD)

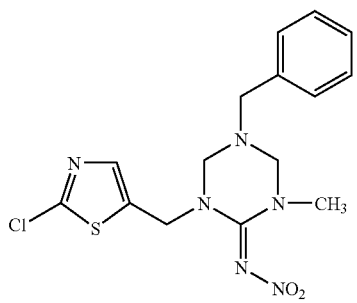

are introduced into 75 ml of butyronitrile and, at 55 to 60° C., 7.9 g (0.22 mol) of gaseous hydrogen chloride are introduced into the suspension with stirring over the course of 20 min. The mixture is after-stirred for a further 1 h at 55 to 60° C., then cooled to 0 to −5° C., and 50 ml of ice-water are added at this temperature. After thorough stirring, the suspension is adjusted to pH=8 at 0 to −5° C. by the addition of dilute sodium hydroxide solution, then after-stirred for 5 min, and then filtered with suction, and the precipitate is washed with about 150 ml of water.

Drying gives a virtually white solid.

| Yield: | 12.1 g (91.2% of theory, 94.7% purity according to HPLC and 94.1% content according to ISTD) |
|---|---|
| $^1$H NMR (DMSO): | δ = 2.80(3H), 4.50(2H), 7.60(1H), 7.94(broad, 1H), 9.17 (broad, 1H) ppm. |
| LC/MS: | 250 [M + H]+, 208, 120 (electrospray, positive mode). |

Example 2

547 g (1.2 mol) of 1-(2-chlorothiazol-5-ylmethyl)-2-nitro-imino-5-benzyl-3-methyl-1,3,5-triazacyclohexane (83.4% strength according to ISTD) are introduced at room temperature into 1145 g of butyronitrile, the mixture is heated to 60° C. and, at this temperature, 181 g (4.9 mol) of gaseous hydrogen chloride are introduced into the suspension with stirring over the course of 60 min. The mixture is after-stirred for a further 1 h at 60° C. and 1080 ml of water are added at this temperature. The temperature falls to 50° C., the solid dissolves completely, and two phases form. The mixture is cooled to 20° C., and the pH is adjusted to 6 by adding concentrated sodium hydroxide solution with stirring. The resulting suspension is cooled to 0° C., filtered with suction and washed in a displacement washer with water at 20° C.

Drying at 50° C. in a vacuum drying cupboard gives a virtually white solid.

Yield: 275 g (91.1% of theory, 99.1% content according to ISTD)

Example 3

22 g (0.05 mol) of 1-(2-chlorothiazol-5-lymethyl)-2-nitro-imino-5-benzyl-3-methyl-1,3,5-triazocyclohexane (86.6% according to ISTD) are introduced into 75 ml of propionitrile, and 8.6 g (0.235 mol) of gaseous hydrogen chloride are introduced into the suspension with stirring at 55 to 60° C. over the course of 20 min. The mixture is after-stirred for a further 1 h at 55 to 60° C., then cooled to 0 to −5° C., and 50 ml of ice-water are added at this temperature. After thorough stirring, the suspension is adjusted to pH=8 at 0 to −5° C. by adding dilute sodium hydroxide solution, after-stirred for 2 h and filtered with suction, and the precipitate is washed with about 120 ml of water.

Drying gives a virtually white solid.

Yield: 11.36 g (88.8% of theory, 98.4% purity according to HPLC and 97.6% content according to ISTD)

Example 4

2 g (0.005 mol) of 1-(2-chlorothiazol-5-ylmethyl)-2-nitro-imino-5-benzyl-3-methyl-1,3,5-triazacyclohexane (95.7% according to ISTD) are introduced into 25 ml of butyronitrile, and, at 0 to 5° C., gaseous hydrogen chloride is introduced into the suspension with stirring to the point of saturation. With slight exothermy, a clear solution immediately forms. The mixture is heated to 80° C., and hydrogen chloride escapes, and after stirring for 2 h at this temperature, a suspension has formed. The suspension is then cooled to 0 to −5° C. and filtered with suction, giving a virtually white solid.

Yield: 1.42 g (95.5% of theory, 84% content according to ISTD)

Comparative example (not according to the invention)

2 g (0.005 mol) of 1-(2-chlorothiazol-5-ylmethyl)-2-nitro-imino-5-benzyl-3-methyl-1,3,5-triazacyclohexane (95.7% strength according to ISTD) are introduced into 40 ml of acetonitrile and, at 0 to 5° C., gaseous hydrogen chloride is introduced into the suspension with stirring until the point of saturation. With slight exothermy, the suspension persists. The suspension is heated to 75° C., and hydrogen chloride escapes, and after stirring for 2 h at this temperature, a clear solution has formed. The solution is then cooled to 0 to −5° C. A solid precipitates out; this is filtered off with suction and washed with some petroleum ether, giving a virtually white solid.

Yield: 1.3 g (43.4% of theory, 41.7% content according to HPLC, 56.8% starting material according to HPLC)

The purity/content determination in the above examples is carried out in accordance with the methods of HPLC. It is possible to work with or without an internal standard (ISTD).

Using a similar method to the above examples, it is also possible to obtain the compounds of the formula (I) given in the table below:

TABLE

| Example No. | Het | R$^1$ | R$^2$ |
|---|---|---|---|
| I-2 | 2-chloropyridin-5-yl | H | H |
| I-3 | 2-chloropyridin-5-yl | H | —CH$_3$ |
| I-4 | 2-chloropyridin-5-yl | H | —C$_2$H$_5$ |
| I-5 | 2-chloropyridin-5-yl | H | —C$_3$H$_7$(n) |
| I-6 | 2-chloropyridin-5-yl | H | cyclopropyl |

TABLE-continued

| Example No. | Het | R¹ | R² |
|---|---|---|---|
| I-7 | 6-chloropyridin-3-yl | H | —C₄H₉(n) |
| I-8 | 6-chloropyridin-3-yl | H | —CH(CH₃)₂ |
| I-9 | 6-chloropyridin-3-yl | H | —CH₂—C₆H₅ |
| I-10 | 6-chloropyridin-3-yl | H | —CH₂-(pyridin-3-yl) |
| I-11 | 6-chloropyridin-3-yl | H | —CH₂-(6-chloropyridin-3-yl) |
| I-12 | 6-chloropyridin-3-yl | H | —CH₂-(4-chlorophenyl) |
| I-13 | 6-chloropyridin-3-yl | —CH₃ | —CH₃ |
| I-14 | 6-chloropyridin-3-yl | —CH₃ | —C₂H₅ |
| I-15 | 6-chloropyridin-3-yl | —CH₃ | cyclopropyl |
| I-16 | 6-chloropyridin-3-yl | —CH₃ | —C₃H₇(n) |
| I-17 | 6-chloropyridin-3-yl | —C₂H₅ | —CH₃ |
| I-18 | 6-chloropyridin-3-yl | —C₂H₅ | —C₂H₅ |
| I-19 | 6-chloropyridin-3-yl | —C₂H₅ | cyclopropyl |

TABLE-continued

| Example No. | Het | R¹ | R² |
|---|---|---|---|
| I-20 | 2-chloro-1,3-thiazol-5-yl | H | H |
| I-21 | 2-chloro-1,3-thiazol-5-yl | H | CH₃ |
| I-22 | 2-chloro-1,3-thiazol-5-yl | H | —C₂H₅ |
| I-23 | 2-chloro-1,3-thiazol-5-yl | H | cyclopropyl |
| I-24 | 2-chloro-1,3-thiazol-5-yl | H | —CH₂—C₆H₅ |
| I-25 | 2-chloro-1,3-thiazol-5-yl | H | —CH₂-(4-chlorophenyl) |
| I-26 | 2-chloro-1,3-thiazol-5-yl | CH₃ | CH₃ |
| I-27 | 2-chloro-1,3-thiazol-5-yl | C₂H₅ | CH₃ |
| I-28 | 2-chloro-1,3-thiazol-5-yl | CH₃ | C₂H₅ |
| I-29 | 2-chloro-1,3-thiazol-5-yl | CH₃ | cyclopropyl |
| I-30 | 6-chloropyridin-3-yl | H | —CH₂—CH=CH₂ |
| I-31 | 6-chloropyridin-3-yl | H | —CH₂—C≡CH |
| I-32 | 2-chloro-1,3-thiazol-5-yl | H | —CH₂—CH=CH₂ |

TABLE-continued

| Example No. | Het | $R^1$ | $R^2$ |
|---|---|---|---|
| I-33 | 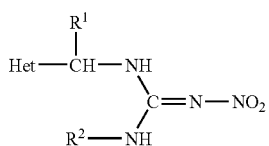 | H | —$CH_2$—C≡CH |
| I-34 | | H | $CH_3$ |
| I-35 | | $CH_3$ | $CH_3$ |

What is claimed is:

1. A process for the preparation of a compounds of the Formula (I)

$$\underset{R^2-NH}{\overset{R^1}{Het-CH-NH}}\!\!\!\!\!\!\!\!\!\!\!\!\!\!\!\!\!\!\!\!\!\!\!\!\!\!\!\!\!\!\!\!\!\!\!\!\!\!\!\!C=N-NO_2 \qquad (I)$$

in which $R^1$ is hydrogen or $C_1$–$C_4$-alkyl, $R^2$ is hydrogen, $C_1$–$C_6$-alkyl, $C_3$–$C_6$-cycloalkyl or a radical —$CH_2R^3$, $R^3$ is $C_2$–$C_5$-alkenyl, $C_2$–$C_5$-alkinyl, phenyl, cyanophenyl, nitrophenyl, halogenophenyl having from 1 to 3 halogen atoms; phenyl substituted by $C_1$–$C_3$-alkyl, $C_1$–$C_3$-halogenoalkyl having from 1 to 7 halogen atoms, $C_1$–$C_3$-alkoxy or $C_1$–$C_3$-halogenoalkoxy having from 1 to 7 halogen atoms; 5-thiazolyl substituted by one to two substituents from the group consisting of $C_1$–$C_3$-alkyl, $C_1$–$C_3$-halogenoalkyl having from 1 to 7 halogen atoms, cyclopropyl, halogenocyclopropyl having from 1 to 3 halogen atoms, $C_2$–$C_3$-alkenyl, $C_2$–$C_3$-alkinyl, $C_1$–$C_3$-alkoxy, $C_2$–$C_3$-halogenoalkenyl having from 1 to 5 halogen atoms, $C_2$–$C_3$-halogenoalkinyl having from 1 to 3 halogen atoms, $C_1$–$C_3$-halogenoalkoxy having from 1 to 7 halogen atoms, $C_1$–$C_3$-alkylthio, $C_1$–$C_3$-halogenoalkylthio having from 1 to 7 halogen atoms, allyloxy, propargyloxy, allylthio, propargylthio, halogenoallyloxy having from 1 to 5 halogen atoms, halogenoallylthio having from 1 to 5 halogen atoms, halogen, cyano or nitro; or 3-pyridyl substituted by one to four radicals from the group consisting of $C_1$–$C_3$-halogenoalkyl having from 1 to 7 halogen atoms, cyclopropyl, halogenocyclopropyl having from 1 to 3 halogen atoms, $C_2$–$C_3$-alkenyl, $C_2$–$C_3$-alkinyl, $C_2$–$C_3$-halogenoalkenyl having from 1 to 5 halogen atoms, $C_2$–$C_3$-halogenoalkinyl having from 1 to 3 halogen atoms, $C_1$–$C_3$-halogenoalkoxy having from 1 to 7 halogen atoms, $C_1$–$C_3$-alkylthio, $C_1$–$C_3$-halogenoalkylthio having from 1 to 7 halogen atoms, allyloxy, propargyloxy, allylthio, propargylthio, halogenoallyloxy having from 1 to 5 halogen atoms, halogenoallylthio having from 1 to 5 halogen atoms, cyano, nitro, $C_1$–$C_3$-alkyl, $C_1$–$C_3$-alkoxy or halogen, Het is an unsubstituted or substituted aromatic or non-aromatic, monocyclic or bicyclic heterocyclic radical selected from the series

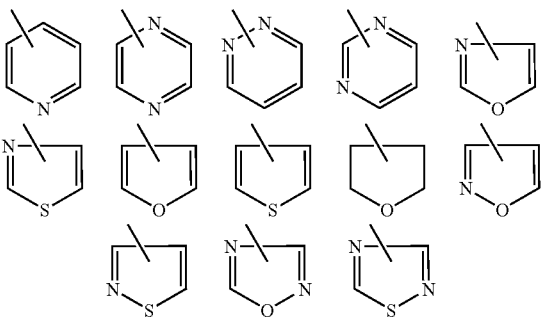

which may include one to two substituents from the group consisting of $C_1$–$C_3$-halogenoalkyl having from 1 to 7 halogen atoms, cyclopropyl, halogenocyclopropyl having from 1 to 3 halogen atoms, $C_2$–$C_3$-alkenyl, $C_2$–$C_3$-alkinyl, $C_2$–$C_3$-halogenoalkenyl having from 1 to 5 halogen atoms, $C_2$–$C_3$-halogenoalkinyl having from 1 to 3 halogen atoms, $C_1$–$C_3$-halogenoalkoxy having from 1 to 7 halogen atoms, $C_1$–$C_3$-alkylthio, $C_1$–$C_3$-halogenoalkylthio having from 1 to 7 halogen atoms, allyloxy, propargyloxy, allylthio, propargylthio, halogenoallyloxy having from 1 to 5 halogen atoms, halogenoallylthio having from 1 to 5 halogen atoms, cyano, nitro, $C_1$–$C_3$-alkyl, $C_1$–$C_3$-alkoxy and halogen, comprising reacting in the presence of a nitrile having from 3 to 5 carbon atoms, a compound of the Formula (II)

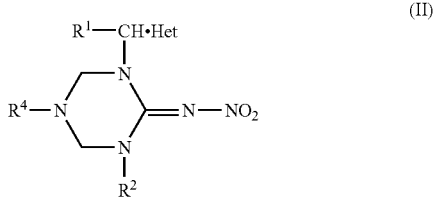

in which $R^1$, $R^2$ and Het are as defined above, and $R^4$ is $C_1$–$C_{10}$-alkyl, $C_3$–$C_6$-cycloalkyl, phenyl, arylalkyl or heterocyclylmethyl, each of which may be unsubstituted or substituted, where heterocyclyl is an unsaturated or saturated 5- or 6-membered heterocycle containing one or more heteroatoms from the series nitrogen, oxygen and sulphur, with an anhydrous hydrogen halide.

2. The process according to claim 1, wherein in the compound of the Formula (II)

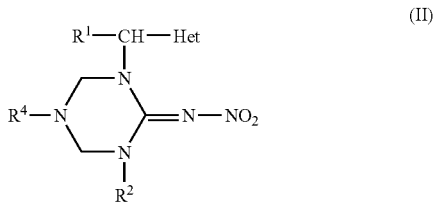

$R^1$ is hydrogen, methyl, ethyl, n- or i-propyl,

R² is hydrogen, methyl, ethyl, n-propyl, i-propyl or n-butyl, cyclopropyl, cyclopentyl, cyclohexyl or a radical —CH₂R³, R³ is $C_2$–$C_5$-alkenyl, $C_2$–$C_5$-alkinyl, phenyl, cyanophenyl, nitrophenyl, halogenophenyl having from 1 to 3 halogen atoms; phenyl substituted by $C_1$–$C_3$-alkyl, $C_1$–$C_3$-halogenoalkyl having from 1 to 7 halogen atoms, $C_1$–$C_3$-alkoxy or $C_1$–$C_3$-halogenoalkoxy having from 1 to 7 halogen atoms; 5-thiazolyl substituted by one to two substituents from the group consisting of $C_1$–$C_3$-alkyl, $C_1$–$C_3$-halogenoalkyl having from 1 to 7 halogen atoms, cyclopropyl, halogenocyclopropyl having from 1 to 3 halogen atoms, $C_2$–$C_3$-alkenyl, $C_2$–$C_3$-alkinyl, $C_1$–$C_3$-alkoxy, $C_2$–$C_3$-halogenoalkenyl having from 1 to 5 halogen atoms, $C_2$–$C_3$-halogenoalkinyl having from 1 to 3 halogen atoms, $C_1$–$C_3$-halogenoalkoxy having from 1 to 7 halogen atoms, $C_1$–$C_3$-alkylthio, $C_1$–$C_3$-halogenoalkylthio having from 1 to 7 halogen atoms, allyloxy, propargyloxy, allylthio, propargylthio, halogenoallyloxy having from 1 to 5 halogen atoms, halogenoallylthio having from 1 to 5 halogen atoms, halogen, cyano or nitro; or 3-pyridyl substituted by one to two radicals from the group consisting of $C_1$–$C_3$-halogenoalkyl having from 1 to 7 halogen atoms, cyclopropyl, halogenocyclopropyl having from 1 to 3 halogen atoms, $C_2$–$C_3$-alkenyl, $C_2$–$C_3$-alkinyl, $C_2$–$C_3$-halogenoalkenyl having from 1 to 5 halogen atoms, $C_2$–$C_3$-halogenoalkinyl having from 1 to 3 halogen atoms, $C_1$–$C_3$-halogenoalkoxy having from 1 to 7 halogen atoms, $C_1$–$C_3$-alkylthio, $C_1$–$C_3$-halogenoalkylthio having from 1 to 7 halogen atoms, allyloxy, propargyloxy, allylthio, propargylthio, halogenoallyloxy having from 1 to 5 halogen atoms, halogenoallylthio having from 1 to 5 halogen atoms, cyano, nitro, $C_1$–$C_3$-alkyl, $C_1$–$C_3$-alkoxy or halogen, R⁴ is unsubstituted $C_1$–$C_{10}$-alkyl or $C_1$–$C_{10}$-alkyl substituted by from 1 to 6 radicals from the group consisting of halogen, hydroxyl, $C_1$–$C_4$-alkoxy, $C_1$–$C_4$-halogenoalkoxy having from 1 to 9 halogen atoms, di-($C_1$–$C_4$-alkyl)-amino or $C_1$–$C_5$-alkoxycarbonyl; unsubstituted $C_3$–$C_6$-cycloalkyl or $C_3$–$C_6$-cycloalkyl substituted by from 1 to 4 radicals from the series $C_1$–$C_4$-alkyl or halogen; in each case unsubstituted phenyl, benzyl or heterocyclylmethyl, or phenyl, benzyl or heterocyclylmethyl each substituted by from 1 to 3 ring substituents from the group consisting of halogen, $C_1$–$C_4$-alkyl, $C_1$–$C_4$-halogenoalkyl having from 1 to 9 halogen atoms, $C_1$–$C_4$-alkoxy, $C_1$–$C_4$-halogenoalkoxy having from 1 to 9 halogen atoms, $C_1$–$C_4$-alkylthio, nitro or cyano, where heterocyclyl is an unsaturated or saturated 5- or 6-membered heterocycle having one or two heteroatoms from the series nitrogen, oxygen and sulphur, Het is an unsubstituted or mono- or disubstituted heterocyclic radical from the series

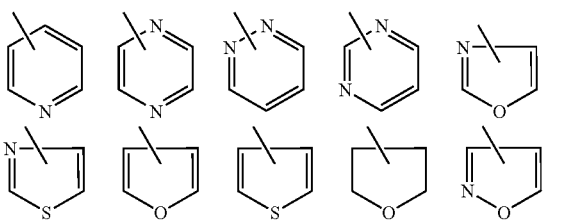

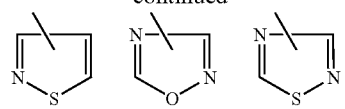

the substituents being chosen from the series fluorine, chlorine, bromine, methyl, ethyl, methoxy and ethoxy.

3. The process according to claim 1, wherein in the compound of the Formula (II)

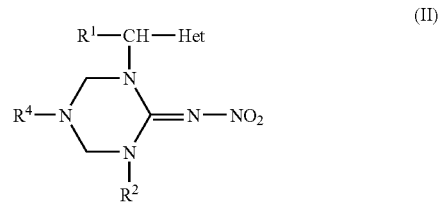

R¹ is hydrogen, methyl or ethyl,

R² is hydrogen, methyl, ethyl, n-propyl, i-propyl, n-butyl, cyclopropyl, cyclopentyl, cyclohexyl or a radical —CH₂R³, R³ is $C_2$–$C_3$-alkenyl, $C_2$–$C_3$-alkinyl, phenyl, cyanophenyl, nitrophenyl, halogenophenyl having from 1 to 3 halogen atoms; phenyl substituted by $C_1$–$C_3$-alkyl, $C_1$–$C_3$-halogenoalkyl having from 1 to 7 halogen atoms, $C_1$–$C_3$-alkoxy or $C_1$–$C_3$-halogenoalkoxy having from 1 to 7 halogen atoms; 5-thiazolyl or 3-pyridyl each substituted by one or two substituents from the group consisting of $C_1$–$C_3$-alkyl, $C_1$–$C_3$-halogenoalkyl having from 1 to 7 halogen atoms, $C_1$–$C_3$-alkoxy, $C$–$C_3$-halogenoalkoxy having from 1 to 7 halogen atoms, $C_1$–$C_3$-alkylthio, $C_1$–$C_3$-halogenoalkylthio having from 1 to 7 halogen atoms, halogen, cyano or nitro, R⁴ is $C_1$–$C_{10}$-alkyl; $C_1$–$C_8$-alkyl, substituted by from 1 to 6 radicals from the group consisting of halogen, $C_1$–$C_4$-alkoxy and $C_1$–$C_4$-halogenoalkoxy having from 1 to 9 halogen atoms; unsubstituted $C_3$–$C_6$-cycloalkyl or $C_3$–$C_6$-cycloalkyl substituted by 1 or 2 radicals from the series methyl, ethyl, fluorine and chlorine; unsubstituted phenyl, benzyl or heterocyclylmethyl, or phenyl, benzyl or heterocyclylmethyl each substituted by from 1 to 3 ring substituents from the group consisting of halogen, $C_1$–$C_4$-alkyl, $C_1$–$C_4$-halogenoalkyl having from 1 to 9 halogen atoms, $C_1$–$C_4$-alkoxy, $C_1$–$C_4$-halogenoalkoxy having from 1 to 9 halogen atoms, $C_1$–$C_4$-alkylthio, nitro or cyano, where heterocyclyl is an unsaturated or saturated 5- or 6-membered heterocycle containing one heteroatom from the series nitrogen, oxygen and sulphur, Het is thiazolyl, pyridyl or tetrahydrofuranyl, each of which may be unsubstituted or mono- or disubstituted the substituents being chosen from the series fluorine, chlorine, methyl and methoxy.

4. The process according to claim 1, wherein in the compound of the Formula (II)

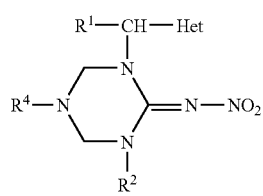

(II)

R[1] is hydrogen, methyl or ethyl,

R[2] is hydrogen, methyl, ethyl, n-propyl, i-propyl, n-butyl, cyclopropyl, cyclopentyl, allyl, propargyl, benzyl, p-chlorobenzyl, 3-pyridylmethyl or 6-chloro-3-pyridylmethyl, R[4] is methyl, ethyl, n-propyl, cyclopropyl, cyclopentyl, cyclohexyl, phenyl, benzyl or furfuryl, Het is one of the radicals.

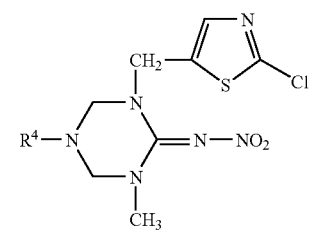

5. The process according to claim 1, wherein in the compound of the Formula II is a compound of the Formula (IIa)

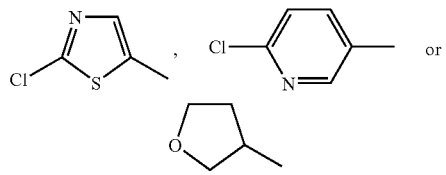

(IIa)

in which

R[4] is as defined in claim 1.

6. The process according to claim 1, wherein in the compound of the Formula II is a compound of the Formula (IIb)

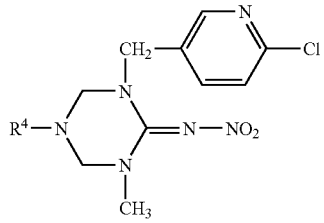

(IIb)

in which

R[4] is as defined in claim 1.

7. The process according to claim 1, wherein the compound of the Formula II is a compound of the Formula (IIc)

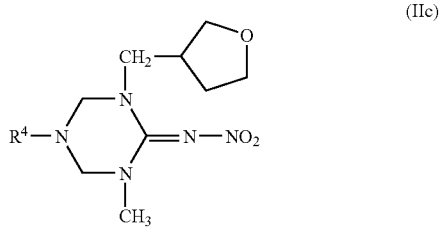

(IIc)

in which

R[4] is as defined in claim 1.

8. The process according to claim 1, wherein the reaction is carried out in the presence of an aliphatic mono- or dinitrile having 3 to 5 carbon atoms.

9. The process according to claim 8, wherein the nitrile is selected from the group consisting of propionitrile, butyronitrile, valeronitrile, malononitrile, succinonitrile and glutaronitrile.

10. The process according to claim 9, wherein the nitrile is propionitrile or butyronitrile.

11. The process according to claim 10, wherein the nitrile is butyronitrile.

12. The process according to claim 1, wherein the anhydrous hydrogen halide is selected from the group consisting of hydrogen chloride, hydrogen bromide hydrogen iodide.

13. The process according to claim 12, wherein the anhydrous halogen halide is hydrogen chloride or hydrogen bromide.

14. The process according to claim 13, wherein the anhydrous hydrogen halide is hydrogen chloride.

15. The process according to claim 1, wherein said process is carried out at a temperature between −10° C. and 200° C.

* * * * *